(12) United States Patent
Comley et al.

(10) Patent No.: US 6,652,809 B1
(45) Date of Patent: Nov. 25, 2003

(54) APPARATUS FOR PERFORMING PHOTOMETRIC ASSAYS

(75) Inventors: John Charles William Comley, Turku (FI); Coulton Heath Legge, Ware (FI); Li Qun Lang, Ware (FI)

(73) Assignee: Glaxo Research and Development Limited (GB)

( * ) Notice: Subject to any disclaimer, the term of this patent is extended or adjusted under 35 U.S.C. 154(b) by 0 days.

(21) Appl. No.: 09/508,834

(22) PCT Filed: Sep. 15, 1998

(86) PCT No.: PCT/EP98/05838

§ 371 (c)(1),
(2), (4) Date: May 26, 2000

(87) PCT Pub. No.: WO99/13986

PCT Pub. Date: Mar. 25, 1999

(30) Foreign Application Priority Data

Sep. 17, 1997 (GB) ................................................ 9719673

(51) Int. Cl.$^7$ ............................................... G01N 21/29
(52) U.S. Cl. ...................... 422/82.05; 422/55; 422/58; 422/82.08; 422/82.09; 422/99; 422/102; 436/164; 436/165; 436/172
(58) Field of Search ........................... 422/55, 58, 68.1, 422/73, 82.05, 82.08, 82.09, 99, 102; 436/164, 165, 172

(56) References Cited

U.S. PATENT DOCUMENTS

| 5,277,780 | A | | 1/1994 | Kambara |
| 5,324,401 | A | | 6/1994 | Yeung et al. |
| 5,366,608 | A | | 11/1994 | Kambara |
| 5,483,075 | A | | 1/1996 | Smith et al. |
| 5,498,324 | A | | 3/1996 | Yeung et al. |
| 5,516,409 | A | | 5/1996 | Kambara |
| 5,541,420 | A | | 7/1996 | Kambara |
| 5,560,811 | A | | 10/1996 | Briggs et al. |
| 5,776,078 | A | * | 7/1998 | Wardlaw ..................... 600/576 |
| 5,840,573 | A | * | 11/1998 | Fields ..................... 435/287.2 |
| 5,858,194 | A | * | 1/1999 | Bell ............................ 204/601 |
| 5,976,896 | A | * | 11/1999 | Kumar et al. ................ 436/527 |
| 6,027,695 | A | * | 2/2000 | Oldenberg et al. .......... 422/102 |
| 6,063,251 | A | * | 5/2000 | Kane et al. .................. 204/601 |
| 6,306,578 | B1 | * | 10/2001 | Schellenberger et al. ...... 435/4 |
| 6,376,256 | B1 | * | 4/2002 | Dunnington et al. ........ 436/178 |

FOREIGN PATENT DOCUMENTS

| EP | 0581412 A2 | 2/1994 |
| EP | 0581413 A2 | 2/1994 |
| EP | 0619483 A1 | 10/1994 |
| EP | 0723149 A2 | 7/1996 |
| WO | WO93/05390 | 3/1993 |
| WO | WO93/17325 | 9/1993 |
| WO | WO94/29712 | 12/1994 |
| WO | WO94/29713 | 12/1994 |
| WO | 9511437 | 4/1995 |
| WO | WO95/11450 | 4/1995 |
| WO | 9521382 | 8/1995 |

* cited by examiner

*Primary Examiner*—Jill Warden
*Assistant Examiner*—Dwayne K Handy
(74) *Attorney, Agent, or Firm*—Nixon & Vanderhye PC

(57) ABSTRACT

There is provided according to the invention an apparatus for the performance of photometric assays comprising: 1. A housing; 2. A plurality of translucent capillaries each being sealed at one end; 3. Means to provide each capillary with photonic isolation from a neighbouring capillary; and 4. Optical instrumentation and circuitry adapted to read an optical response or event in each capillary.

25 Claims, 7 Drawing Sheets

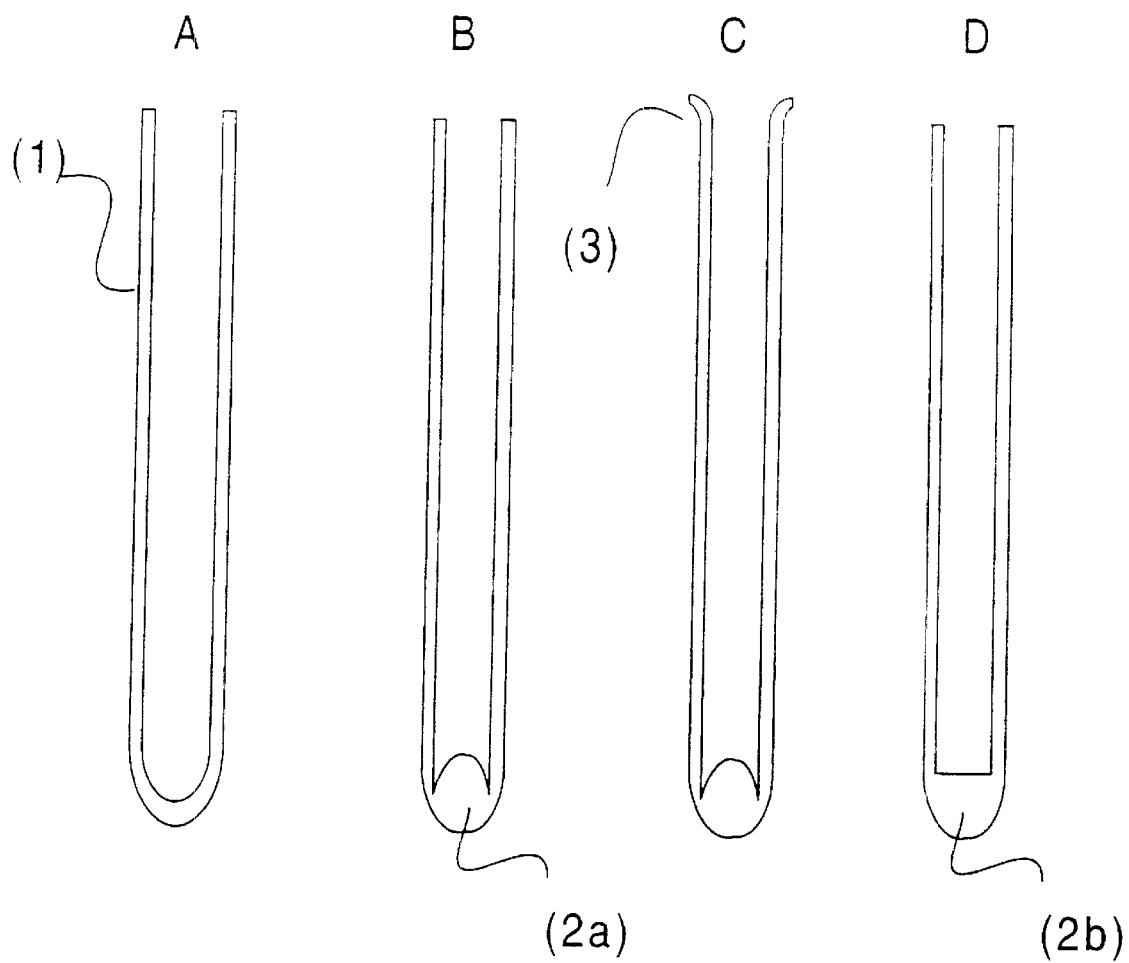

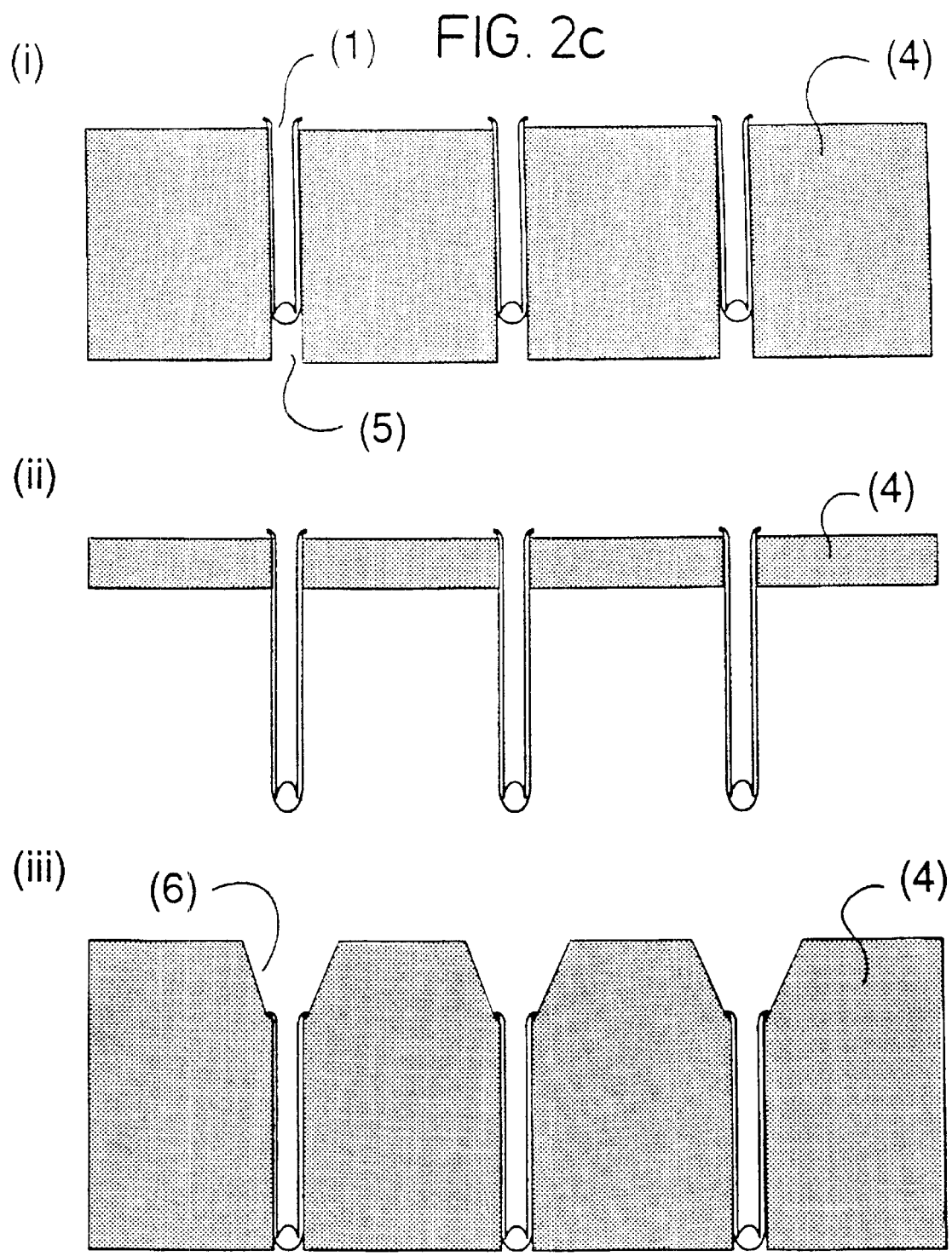

FIG. 6a
Black Microplate            Capillary Array
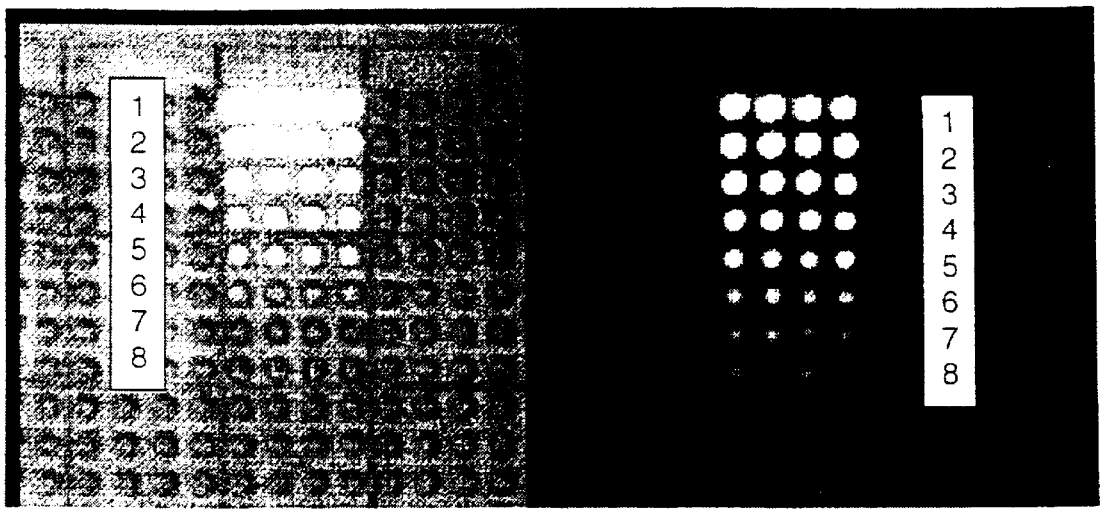
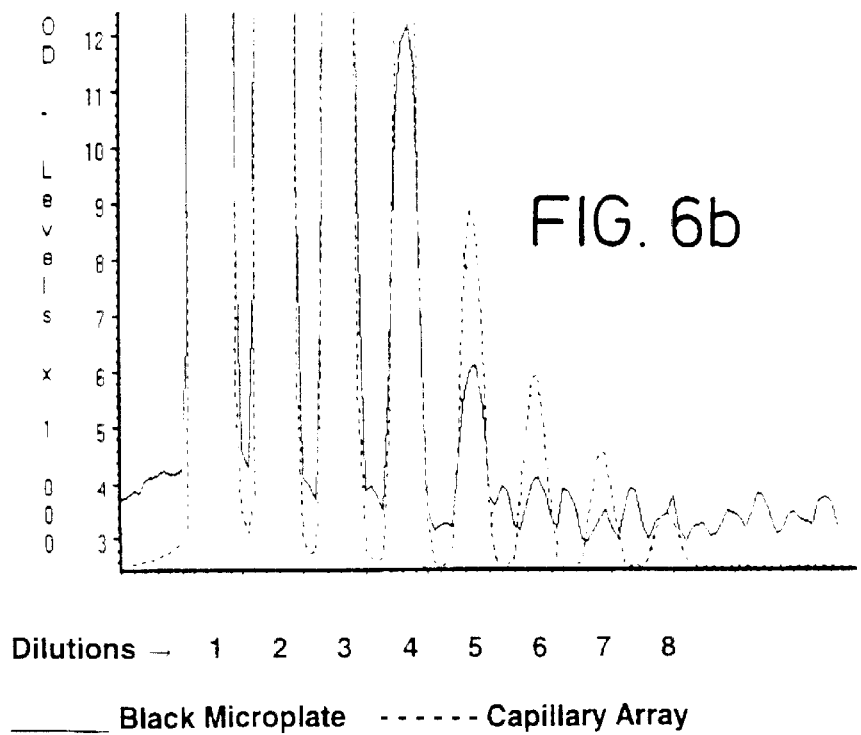
FIG. 6b
Dilutions → 1 2 3 4 5 6 7 8
——— Black Microplate     - - - - - - Capillary Array

APPARATUS FOR PERFORMING PHOTOMETRIC ASSAYS

This invention relates to a novel apparatus for performing photometric assays, especially biochemical photometric assays.

Conventionally photometric assays are performed in microtitre plates comprising 96, 384, 864 or even 1536 wells (8×12, 16×24, 24×36 and 32×48, respectively). The geometry of such plates has become standardised in order to enable photometric readings based on the principles of absorbance, fluorescence, luminescence, phosphorescence or scattering to be made by a plate reading machine on all the wells within a standard format. Such assay systems suffer from the disadvantage that the volume of sample required can be relatively large and the concentration of the substance to be assayed relatively high which increases costs. Furthermore, as assay volumes decrease, systems which do not provide for covering or sealing become increasingly prone to evaporation.

There remains a desire to miniaturise photometric assay systems to make possible the assaying of samples of smaller volume while retaining sensitivity and adequate signal-to-noise.

We have now invented an apparatus which permits the performance of photometric assays at high density and low volume with significantly greater sensitivity than has been possible hitherto and with significantly lessened problem of evaporation. Other advantages of our apparatus, such as reduced interference between signals from samples will become apparent from the foregoing.

Thus, according to the invention we provide an apparatus for the performance of photometric assays comprising:
1. A housing;
2. A plurality of translucent capillaries each being sealed at one end;
3. Means to provide each capillary with photonic isolation from a neighbouring capillary; and
4. Optical instrumentation and circuitry adapted to read a photonic response or event in each capillary.

The housing may be manufactured of any rigid material, such as plastics (e.g. perspex) or metal (e.g. steel, aluminium). The housing will serve to retain the capillaries in the desired orientation for reading by the optical instrumentation and circuitry.

Preferably the plurality of translucent capillaries will be arranged in a regular orientation. For example they may be arranged in the housing in arrays of 8×12, 16×24, 32×48, 64×96 (especially when this conforms to the conventional microplate format) or any other desired geometrical arrangement.

Alternatively (although this is not preferred) they may be close packed, in which case they will preferably be close packed into a regular shape, such as a square, rectangle, hexagon or circle. The close packed arrangement may then be retained in the housing.

Capillaries will generally be of circular section, typically having internal and external dimensions in the range 0.1–4 mm e.g. 0.8 mm and 1.0 mm respectively. Capillaries will have a length in the range 1–50 mm e.g. 10 mm.

Capillaries may also have internal and external geometries other than circular. For example, a hexagonal outer section might be an advantageous geometry for close packing.

Preferably, when the capillaries are arranged in arrays, the means to provide each capillary with photonic isolation from a neighbouring capillary is provided when the part of the housing retaining the capillaries comprises a support block in which is manufactured holes, ideally in a regular arrangement, each hole capable of receiving and retaining a single capillary.

The material of manufacture of the housing should not contribute a significant background signal for the assay method used and should not permit transmission of signal from one capillary to the next ("cross-talk") to any significant extent.

Preferably the support block will be manufactured of a light impervious, e.g. a plastics material, such as perspex or high density polypropylene or polytetrafluoroethylene material which may be coloured black. The entire housing may be manufactured of the same material.

For fluorescence applications, the support block will preferably be impervious to light at the emission wavelength even if it is not impervious to light at the excitation wavelength.

For fluorescence applications, the material of manufacture of the support block will preferably have low intrinsic fluorescence.

Capillaries may be arranged in the support block in a density of typically 1–10,000/cm$^2$. Capillaries arranged in arrays of 96, 384 and 1536 will generally be arranged with a separation of 9, 4.5 and 2.25 mm respectively.

The end of the capillary retaining or intending to retain the sample may protrude beyond or be held within the support block. Preferably it will protrude beyond the support block.

We prefer the end of the capillary to be sealed to form a fused bulb.

When the capillaries are close packed the means to provide each capillary with photonic isolation from a neighbouring capillary may be provided by coating each capillary with a light impervious material. Alternatively they may be provided with a coating which is highly internally reflective such as a silver or aluminium coating.

Generally the coating will be a plastics coating. The coating should be sufficiently thick and dense and the material will have properties suitable for the application. For fluorescence applications it will preferably have low intrinsic fluorescence. Frequently the coating will be of a black plastics material.

It is also envisaged that capillaries coated with a light impervious material may be retained in a housing comprising a support block which need not be made of a light impervious material.

In an alternative embodiment, when the capillaries are arranged in arrays the means to provide each capillary with photonic isolation from a neighbouring capillary may comprise an air space. The capillaries will nevertheless be connected through the housing in order to retain them in the desired orientation although these connections will be such that no significant cross-talk occurs.

In one refinement of this embodiment, the capillaries may be considered to be retained in a support block in the sense that the support block rigidly retains them in a fixed orientation, save that the part of the capillary containing or intended to contain a liquid sample is not retained within the support block but is surrounded by air space.

The means for providing each capillary with photonic isolation from a neighbouring capillary may also comprise an air space together with a capillary coating of light impervious material.

Performance of an assay will involve dispensing liquid into one or more capillaries. This may be performed manually but will preferably be performed by an automated system.

Frequently it will be necessary to dispense a sample to be assayed of smaller volume and an assay reagent of larger volume but it may also be necessary to dispense a sample of larger volume. In any event the liquid to be dispensed in the capillary may be dispensed in one or more aliquots which may range in volume from small (nanoliter to picoliter range) to large (microliter range).

Each aliquot may be administered by standard contact dispensing methods, e.g. syringe needle, pipette tip or transfer pin. A sample may be administered to the bottom of the capillary using a microinjection needle but will preferably be administered towards the top of the capillary and encouraged to the bottom of the capillary, e.g. by vibration, taking advantage of surface coatings or geometrical features, by use of pressure differentials or, preferably, by centrifugation.

Centrifugation has the further advantage that it enhances sample mixing.

Centrifugation may be performed using conventional apparatus, e.g. a conventional microplate centrifuge. The shape of the housing may be adapted to assist centrifugation.

Apparatus (e.g. 96, 384 or 1536 multi-channel dispensers) may be used which enables a number of arranged aliquots to be dispensed simultaneously.

Aliquots may also be dispensed by non-contact dispensing, e.g. using piezoelectric or solenoid valve dispenser. This method is more suitable for dispensing smaller volumes (nanoliter to picoliter range).

Typical total aliquot volumes that will be dispensed to a capillary are in the range 0.1–10 $\mu$l, e.g. 1 $\mu$l.

When capillaries are arranged in arrays, each may be provided with a flanged end, opening to an orifice size greater than that of the capillary in order to assist administration of a sample. When the external dimension of the capillary is 1.0 mm, we have found that a flange extending to 1.2 mm is very suitable.

Alternatively or additionally, each capillary may be retained in a support block which is provided with a liquid entry feature adapted to funnel liquid into each capillary. The funnelling arrangement of the liquid entry feature may comprise a moulded cone having an open end of larger diameter than the internal diameter of the capillary in order to assist dispensing of sample. A size comparable to that of conventional microtitre plates thus enabling conventional dispensing equipment (e.g. multichannel 96 or 384 dispensers) to be used is particularly advantageous.

The support block may provide a funnelling arrangement both in embodiments when the part of the capillary containing or intending to contain a liquid sample is retained within the support block and in embodiments when such part is not retained within the support block but is surrounded by air space.

When a capillary with a flange is used together with a support block having a funnelling arrangement, the flange may advantageously serve the further purpose of supporting and sealing the capillary in the support block.

Capillaries may be manufactured from a range of translucent materials, e.g. plastics (such as perspex), glasses (such as fused silica) and quartz. It is preferred that the material gives a low background reading in the optical assay method used. Glasses and quartz are especially preferred, particularly fused silica which demonstrates low phosphorescence.

Without being limited by theory, we believe that the sensitivity of the apparatus arises in greater part since the capillary wall acts as an optical waveguide which very efficiently couples and pipes light out from the enclosed liquid. Preferably a photonic response or event in each capillary is read at its sealed end i.e. light (e.g. fluorescence or luminescence) is collected preferentially from the surface of the sealed end rather than from the liquid surface. Furthermore, when the sealed end forms a fused bulb (as is preferred) it may act as a lens capable of concentrating and focussing light transmitted through the capillary wall, generally at its tip or at a focal point below its tip, preferably onto a single or multiple focal plane. The bulb may present a range of geometries to the internal surface e.g. concave, convex or flat.

A further advantage of the system is that imaging the focal plane of the bulbs in an array may eliminate the parallax/shadowing problems which are seen when imaging conventional microtitre wells. Additionally it may significantly enhance the signal-to-noise ratio (contrast).

The purpose of the light impervious barrier between capillaries is to eliminate or substantially reduce "cross-talk" or interference in signal between one capillary and another.

In the foregoing, the arrangement of the plurality of capillaries will be called a "capillary array".

Capillary arrays may be read using conventional technology for the performance of photometric assays. Any assay in which photons of light are emitted can be used. Typically assays include absorbance assays, fluorescence assays, luminescence assays, phosphorescence assays and assays based on scattering (e.g. Raman or Nephelometry) in liquids containing particles.

For fluorescence applications, the fluorescence signal may be generated by one or more fluorophores attached onto target molecules or within target molecules (autofluorescence). Such fluorescence may be induced by processes involving one or more photons.

The method is suitable for the performance of all types of photometric assay, such as biochemical, chemical and immunological assays etc.

For absorbance assays it would be usual to illuminate the surface of the liquid in each capillary with light and measure transmitted light at the surface of the sealed end of the capillary or at the focal point below the sealed end when the end demonstrates a lens effect. Measurement will consist of measuring the number of photons transmitted at a fixed wavelength. Alternatively absorbance spectra may be measured over a range of wavelengths.

For fluorescence assays one possible arrangement is similar to that described above for absorbance assays, i.e. such that the liquid is illuminated with light of a fixed wavelength and the emitted light is measured from the surface of the sealed end of the capillary or at its focal point. Measurement will consist of measuring the number of photons emitted at a fixed wavelength which will generally be a different wavelength from that of the exciting light. Alternatively, the number of photons emitted over a range of wavelengths may be measured.

Excitation of the sample can, in principal, be achieved by illumination of the sample from any angle. Generally we prefer to illuminate the surface of the liquid enclosed in the capillary from the open end, although the sample may also be excited by illuminating the sealed end of the capillary instead of the liquid surface.

It is envisaged, although not preferred, that the sample may be illuminated from the side e.g. through a support block that is made of or comprises a light transmitting material. In one possible arrangement (as indicated above), the support block may be manufactured of a material which is impervious to light at the emission wavelength but which transmits light at the excitation wavelength thus enabling the sample to be illuminated at the side whilst minimising or eliminating cross-talk. The sample may also be illuminated from the side by an arrangement which includes a light-guide.

Measurement of the fluorescence light may be made immediately after excitation or after a time-delay. Because most background signals are short lived, the use of fluorescent labels with a long lifetime e.g. 10–1000 ns allows time-resolved detection for the reduction of background interference.

The capillary arrangement described may be useful in enabling the miniaturisation of those assay methodologies that use time-resolved fluorescence (including lifetime fluorescence) e.g. Packard Biosciences homogeneous time-resolved fluorescence (HTRF) or Wallac lanthanide chelate excitation technology (LANCE).

For luminescence assays, luminescence will generally be generated by chemical or biological means. For chemiluminescent applications, the light measured arises as a result of a chemical reaction such as the interaction of a radioactive substance with a scintillant. An example of such an application is a scintillation proximity assay. Generally most or all emitted light will be collected; measurement is made of the light emitted at the surface of the sealed end of the capillary or at its focal point. The scintillant may be in the form of a bead and interaction with the radioactive substance may be encouraged by linking the bead to an antibody having affinity for the radioactive substance.

In a particularly advantageous arrangement for performance of a scintillation proximity assay, the scintillant may be coated onto the inside surface of the capillary and the emitted light may be piped through the capillary wall to the sealed end with particularly high efficiency.

Coating may be achieved by any known means, for example by Langmuir Blodgett self assembling monolayers.

The surface of the capillary may also be coated or treated to provide desired characteristics, e.g. to alter the wetting properties of the capillary or by applying a tissue culture treatment to the internal surface to enhance cell adhesion.

For bioluminescent applications, light may be generated by enzyme reaction, e.g. by reaction of luciferase.

A wide range of luminescent assays may be performed by coupling a reaction event to a light generating event based on chemical or biological principles.

For phosphorescence assays, arrangements as described for fluorescent assays will be suitable save that photons of emitted light will be collected and measured over a period of time, e.g. 0.1–10 milliseconds.

For assays based on light scattering in liquids containing particles, a number of arrangements are possible in which the scattered light may be measured directly or indirectly. For example the liquid in each capillary may be illuminated from the side by light and scattered light deflected towards the sealed end of a capillary may be collected and measured from the surface of the sealed end or at its focal point. Measurement will consist of measuring the number of photons collected which may have the same or a different wavelength profile to that of the illuminating light. Alternatively the surface of the liquid in each capillary may be illuminated from the open end and the light which is not scattered and deflected towards the source may be collected and measured from the surface of the sealed end or at its focal point.

As discussed above, detection optics will preferably be focused on the sealed end of the capillary and when this forms a fused bulb, at its tip or at its focal point when it exhibits the lens effect described above.

Performance of the assay may be undertaken with the capillary array in any orientation. Although it may well be preferred to perform assays with the array upright, they may equally well be performed with the array inverted since in this case the sample will be retained at the sealed end by capillary action.

When the geometry of the capillary array is the same as that of conventional microplates (i.e. 8×12, 16×24 and 32×48 arrays, with capillary separation of 9 mm, 4.5 mm and 2.25 mm respectively) conventional microplate readers and imagers may be used with minimal modification.

An example method of excitation for fluorescence assays is with a Xenon flash lamp with an appropriate excitation filter e.g. one in the range 300–700 nm. A filter band width of 10 nm or less will be preferred. Generally mesurement of detected light will be made after passage of the light through an appropriate emission filter.

Photon collection measurements will generally be made with a photomultiplier tube, photodiode or charged coupled device.

Generally photon collection will be performed on each capillary sequentially which will involve providing means to move the detector or the capillary array from one location to another. However when photon collection is performed with a charge coupled device, it may be possible to collect photons in some or all capillaries simultaneously which has obvious advantages in terms of speed of reading and mechanical simplicity. Such a system maximises the advantages of the invention in terms of the ability to measure efficiently very large numbers of samples without significant time restraint.

When the part of the capillary in an array containing or intended to contain a sample is surrounded by air-space, the array may be immersed within a liquid or heat-transfer medium for thermal cycling applications.

As a further aspect of the invention we provide a capillary array comprising

1. A plurality of translucent capillaries each being sealed at one end; and
2. Means to provide each capillary with photonic isolation from a neighbouring capillary.

We also provide such a capillary array wherein the capillaries are retained in a support block in which is manufactured holes, ideally in a regular arrangement, each hole capable of receiving and retaining a single capillary.

We also provide such a capillary array wherein the capillaries are close packed and retained in a housing.

Other features of the capillary array will be apparent from the foregoing.

The invention will be illustrated by reference to the following figures in which:

FIG. 1 shows four example capillary designs;

FIG. 2b shows a view from above of the capillary array of FIG. 2a;

FIG. 6a shows a comparison of the fluorescence image of fluorescein samples in an embodiment of the invention and a conventional microplate.

FIG. 6b shows a histogram of the fluorescence intensity of fluorescein samples in an embodiment of the invention as compared with a conventional microplate.

In FIG. 1, capillaries (1) are shown which (A) have an ordinary sealed end with a concave internal surface geometry, (B) are sealed at one end to form a fused bulb with a convex internal surface geometry (2a), (C) may contain a flange (3) at the open end and (D) are sealed at one end to form a fused bulb with a flat internal surface geometry (2b).

Figure 2A:
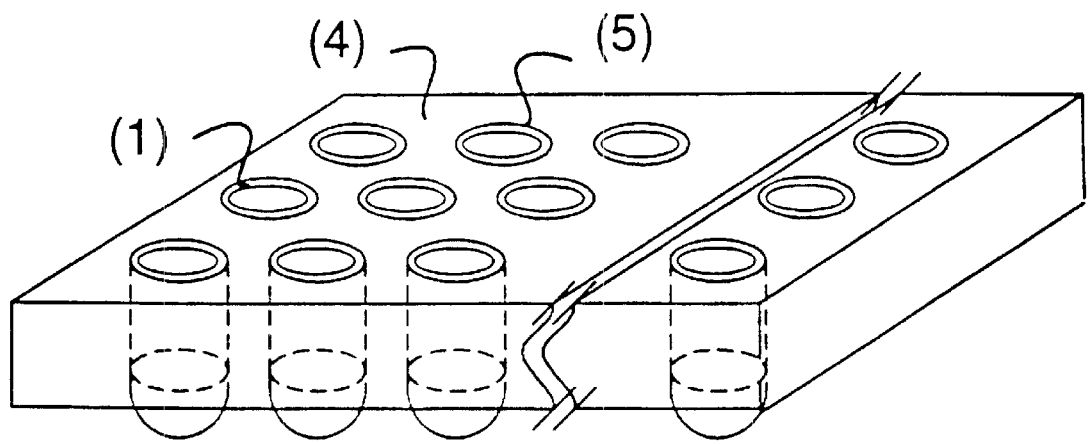
FIG. 2a shows a partial perspective view of a capillary array according to one embodiment of the invention in which the capillary design A of FIG. 1 is illustrated.
Figure 2B:
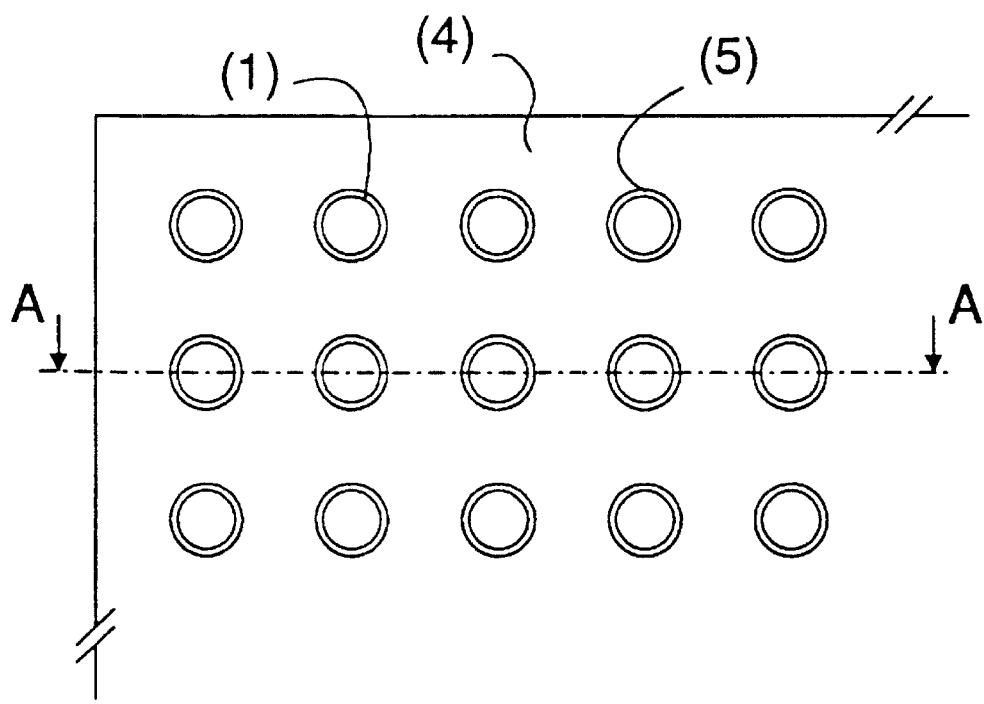
Figure 2C:
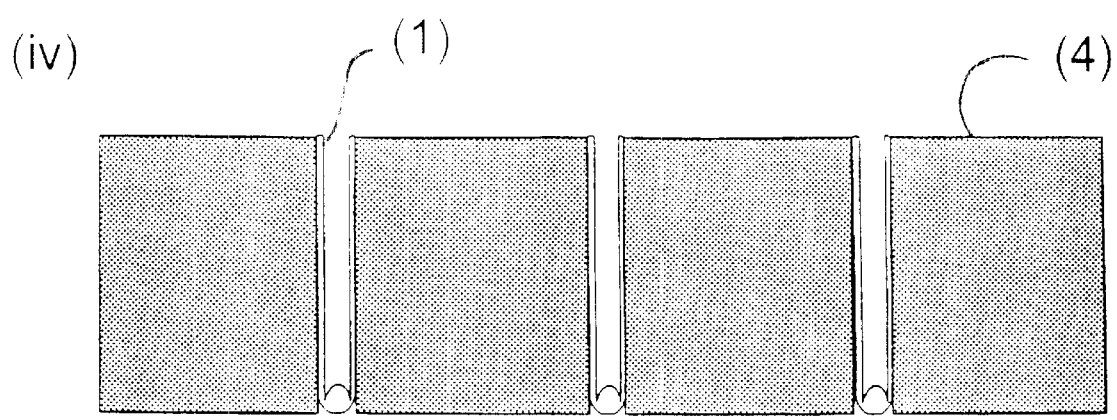
FIG. 2c shows a section along line A—A through the capillary array of FIG. 2a showing four different alternative housings save that capillary design C of FIG. 1 rather than capillary design A is illustrated in embodiments (i) to (iii) and capillary design B of FIG. 1 rather than capillary design A is illustrated in embodiment (iv)

In FIGS. 2a, 2b and 2c, each capillary (1) is retained in a housing (4) comprising a support block in which is formed a hole (5) adapted to receive the capillary. In FIGS. 2c(i) the part of the capillary intended to contain a liquid sample is retained within the support block. In FIG. 2c(ii) the part of the capillary intended to contain a liquid sample is not retained within the support block but is surrounded by air space. FIG. 2c(iii) shows the support block provided with a conical liquid entry feature (6) adapted to funnel liquid into each capillary. FIG. 2c(iv) shows a modification of the embodiment of FIG. 2c(iii) in which the liquid entry feature is absent and the capillary design B of FIG. 1 is used.

Figure 3A:
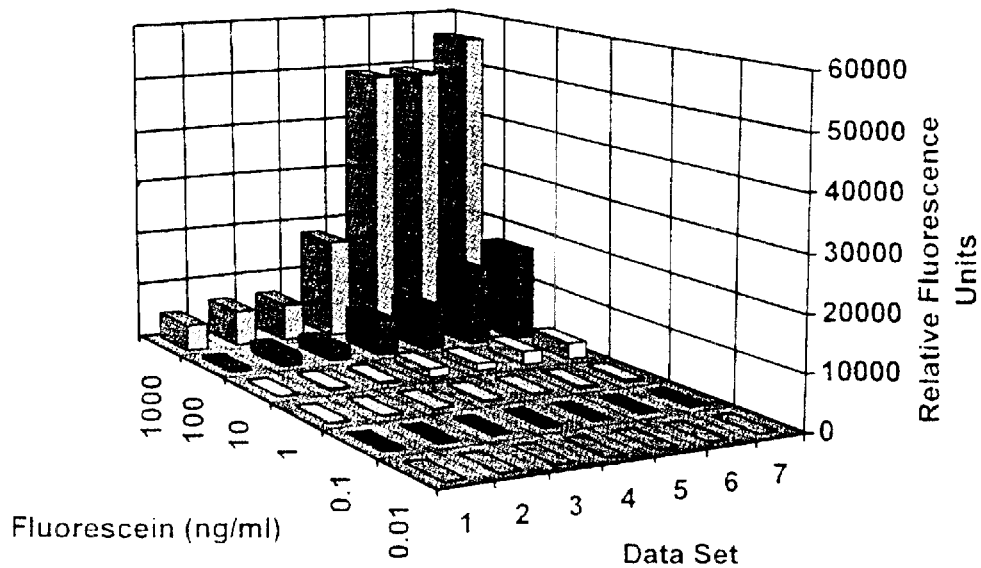
FIGS. 3a and 3b show charts illustrating the sensitivity of an apparatus according to the invention in a fluorescence assay (linear and logarithmic scale respectively)
Figure 3B:
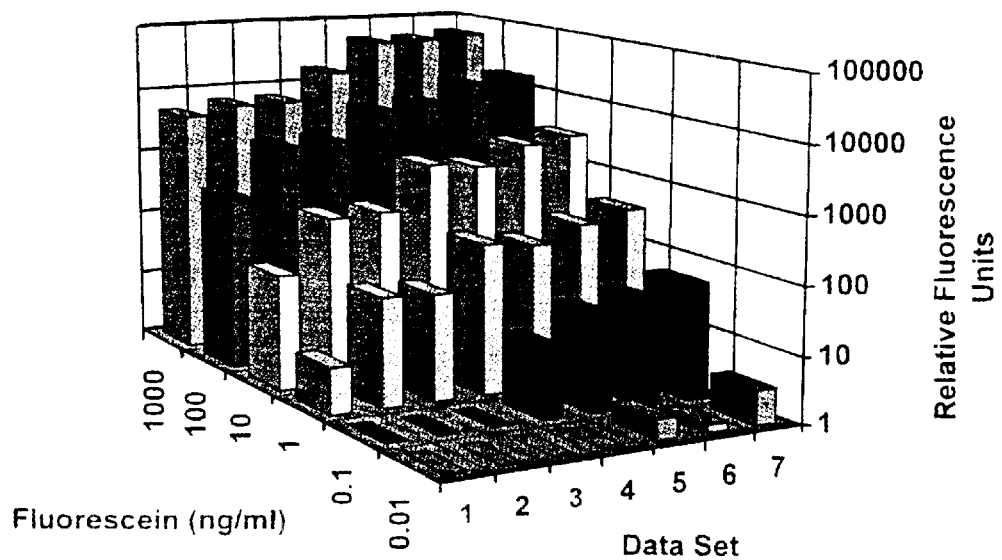

FIGS. 3a and 3b show a comparison of the fluorescent signal (relative fluorescence units) obtained from a range of fluorescein concentrations (0.01 to 1000 ng/ml) when different sample volumes of these fluorescein solutions were measured in various conventional microtitre plate wells (data sets 1, 2, 3, 4, 6 & 7) versus the capillary array, according to the invention (data set 5) in an embodiment resembling that of FIG. 2c(iv). All microtitre plates had wells with opaque black walls and clear base, except for the 864 plate which had clear walls and a clear base. All fluorescent readings were made bottom-up using a single PMT-based fluorescent plate reader at a fixed gain setting with excitation at 485 nm and emission at 535 nm. Readings were corrected for the background on the respective microtitre plates or capillary array.

The data sets listed represent the average of 10 readings from the following conventional microtitre plate wells or capillary array format, together with the sample volume measured:

1: 384 well (16×24) microtitre plate, sample volume 1 $\mu$l.
2: 864 well (24×36) microtitre plate, sample volume 1 $\mu$l.
3: 1536 well (32×48) microtitre plate, sample volume 1 $\mu$l.
4: 864 well (24×36) microtitre plate, sample volume 5 $\mu$l.
5: 384 capillary (16×24) array, according to the invention, sample volume 1 $\mu$l. (Capillary dimensions: 1.0 mm external diameter, 0.8 mm internal diameter, length 10 mm)
6: 96 well (8×12) microtitre plate, sample volume 200 $\mu$l.
7: 384 well (16×24) microtitre plate, sample volume 50 $\mu$l.

FIG. 3a shows that in terms of the total signal collected from the apparatus in a 384 array, sample volume of 1 $\mu$l (data set 5) the invention was comparable to that obtained with a conventional 96 well microtitre plates, sample volume of 200 $\mu$l (data set 7) or to that obtained with conventional 384 microtitre plate, sample volume of 50 $\mu$l (data set 6). All three data sets (5, 6 and 7) showed fluorescent signals at least twice, in many cases four fold greater than 1 or 5 $\mu$l aliquots in 864 or 1536 microplates (data sets 1, 2, 3 and 4).

FIG. 3b shows that the fluorescein concentrations at which significant signal above background can still be detected (absolute sensitivity) extends down to 0.01 ng/ml for the apparatus in a 384 array, sample volume of 1 $\mu$l (data set 5). Comparable sensitivity was also seen with a conventional 96 well microtitre plates, sample volume of 200 $\mu$l (data set 7) and with a conventional 384 microtitre plate, sample volume of 50 $\mu$l (data set 6). All three data sets (5, 6 and 7) had at least 1 (data set 4) or 2 orders of magnitude (data set 1, 2 and 3) greater sensitivity than 1 or 5 $\mu$l aliquots in 864 or 1536 microplates (data sets 1, 2, 3 and 4).

Figure 4:
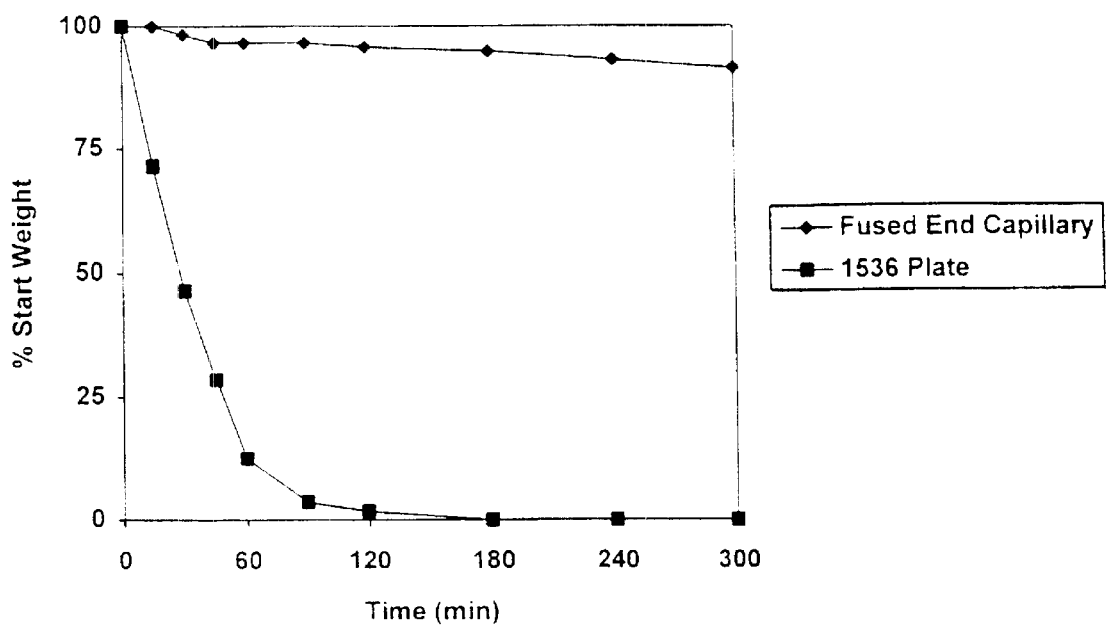
FIG. 4 shows a comparison of the susceptibility to evaporation of an embodiment of the apparatus according to the invention with a conventional apparatus.

FIG. 4 shows a graph of the rate of evaporation of 1 $\mu$l of water from a fused end capillary versus an unsealed 1536 plate. Results expressed as a percentage of the start weight and were determined by repeatedly weighing (to 0.00001 g) either 10 capillaries together (each containing 1 $\mu$l of water at the base of the capillary) or a portion of a 1536 plate (containing ten separate aliquots of 1 $\mu$l of water/well). Evaporation was followed at room temperature and no attempt was made to cover the capillaries or the wells. The results clearly demonstrate the advantage of the capillaries in reducing evaporation in that less than 10% of the water was lost from the capillaries over 5 hours whilst 1 $\mu$l aliquots of water placed within the wells of the 1536 plate had completely evaporated in 3 hours.

Figure 5:
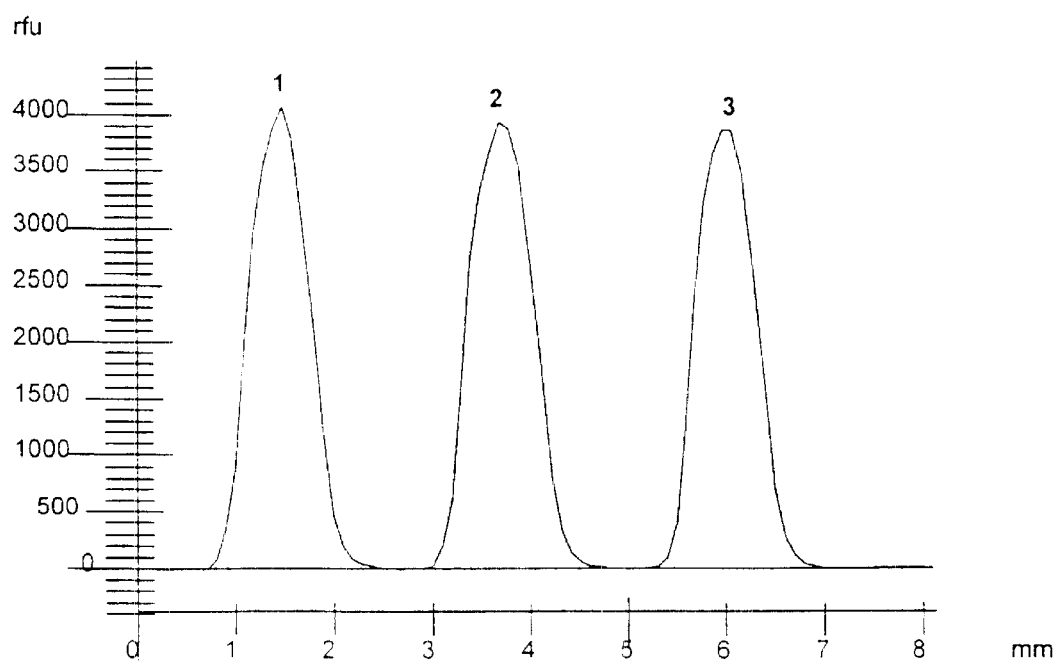
FIG. 5 shows a fluorescence scan of three capillaries in a 1536 capillary array according to the invention.

FIG. 5 shows a scan of the fluorescence emitted from 3 adjacent capillaries in a 1536 (32×48) array having capillary spacing of 2.25 mm in an embodiment of the invention resembling that of FIG. 2c(iv).

It can be seen that there is very little crosstalk in the space between capillaries. Capillary dimensions were: 1.0 mm external diameter, 0.8 mm internal diameter, length 10 mm. The capillary array was imaged with a fluorescence scanning imager and the fluorescence intensity (rfu) integrated along the midline of three adjacent capillaries each containing 1 $\mu$l of a 100 ng/ml solution of fluorescein.

FIGS. 6a and 6b show a comparison of the fluorescent image obtained for a range of fluorescein dilutions when 1 $\mu$l of these solutions were measured in a conventional solid black microplate versus a capillary array, according to the invention in an embodiment resembling that of FIG. 2c(iv). Both the microplate and the capillary array were at 1536 density with 2.25 mm spacing between wells. The concentration of fluorescein in the dilutions were 1—1000 nM, 2—333.3 nM, 3—111.1 nM, 4—37.0 nM, 5—12.3 nM, 6—4.1 nM, 7—1.37 nM and 8—buffer alone. Each dilution was in quadruplicate with dilution 1 to the top of the image, progressing down to dilution 8 at the bottom of the image. In FIG. 6a, the image of the microplate and the capillary array were obtained using a microplate imaging system under identical conditions (10 sec exposure, 4× gain, 2×2 binning, with excitation at 485 nm and emission at 535 nm). Epifluorescent images were obtained by focussing the imager from the upper microplate surface or on the fused end of the capillaries. FIG. 6b shows a histogram of the intensity of the fluorescence signal (OD levels ×1000) along the dilution series of the black microplate or the capillary array.

It can be seen from FIGS. 6a and 6b that the conventional black microplate shows a considerable background signal on imaging mainly due to reflection of fluorescence from the surface of the microplate. In contrast when the capillary array was imaged at the focal plane of capillary bulbs that extended beyond the support block the background is reduced to almost zero. The result is that the signal to noise ratio (contrast) of the capillary array is significantly enhanced over the conventional microplate and it is possible to distinguish lower fluorescein dilutions.

What is claimed is:

1. An apparatus for the performance of photometric assays comprising:
   a housing;
   a capillary array including a plurality of translucent capillaries each being sealed at one end to form a fused bulb; and means providing each capillary with photonic isolation from a neighboring capillary; and
   optical instrumentation and circuitry adapted to read an optical response or event in each capillary.

2. An apparatus according to claim 1, wherein the plurality of translucent capillaries are arranged in a regular orientation comprising one of a square, a rectangle, a hexagon and a circle.

3. An apparatus according to claim 2, wherein the capillaries are arranged in arrays.

4. An apparatus according to claim 3, wherein the capillaries are arranged in arrays of 8×12, 16×24 or 32×48.

5. An apparatus according to claim 1, wherein the capillaries are retained in a support block having holes defined therein, each hole capable of receiving a single capillary.

6. An apparatus according to claim 5, wherein the support block is manufactured of a light impervious material, thereby defining said means providing photonic isolation.

7. An apparatus according to claim 6, wherein the light impervious material is a black plastics material.

8. An apparatus according to claim 5, wherein the support block is manufactured of a material which has low intrinsic fluorescence.

9. An apparatus according to claim 5, wherein the part of the capillary containing or intended to contain a liquid sample is retained within the support block.

10. An apparatus according to claim 5, wherein the part of the capillary containing or intended to contain a liquid sample is not retained within the support block but is surrounded by air space.

11. An apparatus according to claim 1, wherein each capillary is provided with a flanged end.

12. An apparatus according to claim 5, wherein the support block is provided with a liquid entry feature adapted to funnel liquid into each capillary.

13. An apparatus according to claim 12, wherein the funneling arrangement of the liquid entry feature comprises a molded cone.

14. An apparatus according to claim 13, wherein each capillary is coated with a light impervious material, thereby defining said means providing photonic isolation.

15. An apparatus according to claim 14, wherein the light impervious material is black plastics material.

16. An apparatus according to claim 1, wherein the capillary is made of a glass or quartz.

17. An apparatus according to claim 1, wherein the optical response or event in each capillary is read at its sealed end.

18. An apparatus according to claim 1, wherein the bulb exhibits a lens effect capable of concentrating and focusing light transmitted through the capillary wall.

19. An apparatus according to claim 1, wherein the capillaries are coated or surface treated.

20. An apparatus according to claim 1, wherein the capillaries are surface treated by applying a tissue culture treatment to the internal surface to enhance cell adhesion.

21. An apparatus according to claim 1, wherein the optical instrumentation and circuitry is adapted to measure the absorbance of a liquid retained in a capillary.

22. An apparatus according to claim 1, wherein the optical instrumentation and circuitry is adapted to measure the luminescence of a liquid retained in a capillary.

23. An apparatus according to claim 1, wherein the optical instrumentation and circuitry is adapted to excite a liquid retained in a capillary with light and measure the light emitted by fluorescence.

24. An apparatus according to claim 1, wherein the optical instrumentation and circuitry is adapted to excite a liquid retained in a capillary with light and measure the light emitted by phosphorescence.

25. An apparatus according to claim 1, wherein the optical instrumentation and circuitry is adapted to excite a liquid retained in a capillary with light and measure the scattered light directly or indirectly.

* * * * *

UNITED STATES PATENT AND TRADEMARK OFFICE
CERTIFICATE OF CORRECTION

PATENT NO. : 6,652,809 B1
DATED : November 25, 2003
INVENTOR(S) : Comley et al.

It is certified that error appears in the above-identified patent and that said Letters Patent is hereby corrected as shown below:

<u>Title page,</u>
Item [73], Assignee, "Glaxo Research and Development Limited (GB)" should be
-- Glaxo Wellcome Inc. --

Signed and Sealed this

Thirteenth Day of April, 2004

JON W. DUDAS
*Acting Director of the United States Patent and Trademark Office*